United States Patent [19]

Inagaki et al.

[11] Patent Number: 5,630,806

[45] Date of Patent: May 20, 1997

[54] SPIRAL WRAPPED MEDICAL TUBING

[75] Inventors: Tsutomu Inagaki, Lagrangeville, N.Y.;
Gregory A. Gaston, Hixon, Tenn.;
Thomas Eng, Pleasant Valley, N.Y.

[73] Assignee: Hudson International Conductors, Inman, Ga.

[21] Appl. No.: 519,071

[22] Filed: Aug. 24, 1995

Related U.S. Application Data

[63] Continuation of Ser. No. 52,055, Apr. 21, 1993, abandoned, which is a continuation-in-part of Ser. No. 744,318, Aug. 13, 1991, abandoned.

[51] Int. Cl.$^6$ .................................................. A61M 25/00
[52] U.S. Cl. .................................................. 604/282
[58] Field of Search ................................ 604/264, 280, 604/282; 128/656–658, 772

[56] References Cited

U.S. PATENT DOCUMENTS

| | | |
|---|---|---|
| 3,749,085 | 7/1973 | Willson et al. . |
| 4,020,829 | 5/1977 | Willson et al. . |
| 4,676,229 | 6/1987 | Krasnicki et al. .................. 128/4 |
| 4,737,153 | 4/1988 | Shimamura et al. ............. 604/282 |
| 4,976,689 | 12/1990 | Buchbinder et al. ............. 604/95 |
| 5,137,013 | 8/1992 | Chiba et al. ...................... 128/4 |
| 5,174,295 | 12/1992 | Christian et al. ............. 128/772 X |
| 5,180,376 | 1/1993 | Fischell ........................... 604/282 |

*Primary Examiner*—Corrine M. McDermott
*Attorney, Agent, or Firm*—Andrew D. Maslow

[57] ABSTRACT

A radiopaque tube for use as a medical catheter is provided. The tube is preferably formed about a wire mandrel which is subsequently removed to form the lumen of the tube. The tube includes an inner wall layer made from a polymer resin defining the lumen. A spiral wound reinforcement layer of a radiopaque material is wound about the inner wall layer. The spiral wound layer can comprise flat wire or a multiple strands wound about parallel to each other. A polymer resin outer wall layer is laid over said spiral wound radiopaque layer so that the radiopaque layer is embedded between the inner wall layer and the outer surface of the outer wall layer.

2 Claims, 6 Drawing Sheets

SPIRAL WRAPPED MEDICAL TUBING

This application is a continuation of application Ser. No. 052,055, filed on Apr. 21, 1993 now abandoned which is a continuation-in-part of application Ser. No. 744,318 filed Aug. 13, 1991 now abandoned.

BACKGROUND OF THE INVENTION

1. Field of the Invention

This invention relates to polymer resin tubing especially useful for catheters. More particularly, the invention relates to an ultra thin walled polymer resin flexible tubing containing a reinforcement member within the wall and which member gives the tubing a high mechanical strength, crush resistance, hydrostatic pressure capability, and radio-opacity characteristics while maintaining excellent flexibility and circular cross-section.

2. Description of the Prior Art

In general, small diameter resin tubes have been useful in the medical industry as catheters used for dispensing liquids or placing small devices into a patients vascular system. These procedures include spinal anesthesia, introduction of radio-opaque dyes into blood vessels, percutaneous transluminal coronary angioplasty and the like.

The tubes presently used in the medical field are various constructions of extruded fluoropolymers, and non-extrudable resins. These tubes are generally transparent to X-rays and other radiological techniques. For medical procedures requiring radio-opacity these tubes have been made with radiopaque resin compositions. Other tubes have been made with a metallic stylet inserted in the lumen of the tube and affixed to the ends of the tube.

Typically, fluoropolymer tubes are manufactured using a free extrusion. The fluoropolymer is extruded in the form of a hollow tube, then subjected to other processing to cure or sinter the material. This procedure yields satisfactory product, but is difficult to perform for ultra thin walls. Free extrusion of fluoropolymers with ultra thin walls can cause excessive kinking or collapse during processing.

Another method currently employed to manufacture polymer tubes is by coating a metal wire mandrel with the polymer either by extrusion or by dipping in a polymer bath. The tube is formed after the mandrel is withdrawn by elongating the wire to increase its length and decrease its diameter. The tube can then be removed by sliding it off the wire. Tubes manufactured by this technique have excellent interior diameter control. However, tubes with ultra thin wall thickness can still kink or collapse in use.

U.S. Pat. No. 4,925,710 to Buck et al. discloses an ultra thin walled sintered fluoropolymer tubing formed by coating a removable sintered fluoropolymer core and then removing such core. It is suggested that once such tubing is formed, it can be surrounded or jacketed with other layers such as braided metal or a rigid polymeric material.

Medical catheters have been manufactured from fluoropolymers such as polytetrafluoroethylene and related fluoropolymers because of their desirable physical characteristics. In U.S. Pat. No. 4,940,062 to Hampton et al., a guiding member for a catheter is disclosed, which catheter comprises an inner and an outer tube. The inner tube includes a hypotube which is limited to the proximal portion thereof. Secured to the distal end of the hypotube is a high strength polyimide tubular element lined with a lubricous material such as Teflon (polytetrafluoroethylene).

U.S. Pat. No. 4,898,577 to Badger et al. also discloses a guiding catheter with a controllable distal tip utilizing Teflon lined tubular sheath formed of braided or wound aramid fibers. The tubular sheath is surrounded by a polyethylene jacket. U.S. Pat. No. 3,734,139 to Zafiroglu discloses a composite tubing having a Teflon inner layer and a copolymer outer layer of tetrafluoroethylene and hexafluoropropylene. U.S. Pat. No. 4,051,284 to Ohkubo et at. discloses a method for producing heat resistant resin tubes by coating a metal wire with a polyimide.

U.S. Pat. No. 4,027,659 discloses a medical tube formed by extruding of a thermoplastic with an integral stripe portion which includes a powdered conducting metal or an X-ray opaque salt dispersed in the integral stripe. A medical tube made of a plastic material having an X-ray opaque pigment uniformly and homogeneously dispersed therethrough is taught in U.S. Pat. No. 3,608,555 to Greyson.

Other medical tubing made of radiopaque resin compositions are disclosed in U.S. Pat. Nos. 4,722,344, 4,469,483, 4,581,390 and 4,282,876. U.S. Pat. No. 4,796,637 discloses a catheter whose lumen includes a staff having disposed thereon or therein a predetermined number of spaced apart markings of radiopaque material.

Radiopacity, tube strength, kink resistance, crush resistance and flexibility are desirable characteristics for medical catheters. Radiopacity is desired for traceability in the body via X-Ray in procedures involving long range probing through blood vessels, etc., and for locating a catheter which has broken off while inside the body during such procedures. Tube strength is desired to decrease the possibility of catheter breakage especially during insertion and withdrawal into the vascular system. Flexibility is required for navigation of the catheter through the different passages of the vascular system for many medical procedures. Kink and crush resistance is essential for unimpeded or consistent flow rate in applications where liquids are dispensed (anesthesia, dyes, etc.) and for ease of device insertion where the tube is used as a conduit.

To give the tube these combination properties, the polymeric tubes described have been modified. By introducing a metal wire or stylet into the lumen of the tube, and securing it to or embedding it in the interior wall surface of the tube, the tube will be visible through X-ray and other radiological techniques. The stylet also increases the tensile strength of the catheter tube which helps reduce the chance of breakage during insertion and withdrawal. The size or diameter of the stylet varies, but a compromise between visibility under X-ray, strength, flexibility and fluid flow rates must be considered. To allow more cross-section under X-ray, a larger diameter stylet can be used, giving the catheter more strength, but there are disadvantages of decreased flexibility and decreased flow area of the lumen. This results in a stiffer catheter and possibly requires a larger diameter catheter to recover the flow area of the lumen. A larger diameter catheter introduces more trauma to the patient during such procedures, and therefore is less desirable. A finer diameter stylet would not affect fluid flow as much, would not affect flexibility appreciably, but its low cross-section would cause less visibility by X-ray and give the catheter less of a strength improvement. Further, the stylet inside the tube will hamper applications where devices must be passed through the tube.

Medical catheters, especially those with very thin walls, occasionally experience problems of kinking and collapse during these medical procedures. The typical solution to this problem is to increase the wall thickness to strengthen the tube. This results in a larger tube diameter (for same lumen size) and decreases flexibility, both less desirable characteristics. With a stylet attached to the inside of the tube, although kink resistance is improved, crushing of the tube remains a problem.

The instant invention provides improved mechanical strength, crush resistance, hydrostatic pressure capability and radiopacity over the prior art without a significant sacrifice of the desired physical characteristics for a medical catheter.

SUMMARY OF INVENTION

The present invention provides a polymer resin catheter tube containing a spirally wound reinforcement member imbedded within the tube walls. This invention provides an improved tubing suitable for medical uses with increased strength, improved radiopacity, improved resistance to kinking and collapse and improved flow characteristics.

The tube includes an inner wall layer made from a polymer resin defining the lumen. A spiral wound reinforcement layer of a radiopaque material is wound about the inner wall layer so that the radiopaque material does not overlap itself. A polymer resin outer wall layer is laid over said spiral wound radiopaque layer so that the radiopaque layer is embedded between the inner wall layer and the outer surface of the outer wall layer. The spiral wound reinforcement layer can consist of a single strand or multiple strands wound about the inner wall layer at substantially equal distances from each other strand.

The tubing is made by coating a base mandrel, preferably copper wire, with a base coat of a polymer resin. A radiopaque reinforcement member, preferably a flat stainless steel wire or wires, is then applied to the coated mandrel. The use of a flat wire has the added advantage of making it possible to have a thinner wall tube as well as making it possible to maintain a smoother outer surface. The wall of the tube is then built up with a further coating of polymer resin. The mandrel is then removed to form the inner lumen of the catheter tubing.

Preferably the catheter tube is fabricated from a polyimide or fluoropolymer resin such as polytetrafluoroethylene and related fluoropolymers. These are desirable because they are inert to most chemical solvents, are mechanically strong and tough, have exceptional dielectric properties, can be used at high temperatures and have exceptionally low coefficient of friction. These materials are well suited for coatings of wire. Other resin varnishes would be suitable such as polyamides, polyamidimides, polyurethanes, polyesters and the like. Dispersion polymers may also be used as may any polymer material which can be applied to a mandrel and formed into a tube.

Accordingly it is an object of the invention to provide an improved radiopaque medical tubing.

A further object of the invention is to provide a catheter tubing with increased strength of the wall of the tubing.

Yet another object of the invention is to maximize the radiopacity of the catheter tubing. Compared to a similar catheter tube containing a radio-opaque stylet (with equivalent cross-section) the spiral wound radiopaque reinforcement member in this invention will cast a more substantial "shadow". Essentially the greater length of the spirally wound member (per unit length of catheter tube) and the geometry of the helix pattern of the member will impart a larger X-Ray shadow.

Another object of the invention is to provide a catheter tubing with increased resistance to kinking or collapse. The contribution of the strength and the spiral helix pattern of the reinforcement member in this invention imparts greater strength to the tube wall, and distributes the "kinking forces" and any lateral forces over a larger surface area. This results in an increased resistance to kinking or collapse.

A still further object of the invention is to provide improved flow characteristics to the catheter tubing. By incorporating the reinforcement member within the tube wall, this invention does not have the flow restriction of a stylet in the lumen, while still giving the catheter the property of being radio-opaque.

Another object of the invention is to provide retention of circularity and concentricity of the lumen and the outer tube surface of a catheter tubing. In the prior art where a round wire stylet is imbedded on one side of the tube wall, the lumen and outer tube surface is not concentric. The non-circular cross-section and/or the non-concentricity causes the tube to have different flex characteristics in different directions. This results in a catheter with a flexibility bias which may give rise to navigation problems in the patient. In the present invention, the reinforcement member is spirally wound around the tube, and is imbedded in the wall itself. The resulting catheter tube retains circularity of both the lumen and the outer surface, and both are concentric. Thus the biased flex characteristics do not exist in the present invention.

A still further and important object of the invention is to provide increased flexibility to a high strength catheter tubing. The present invention with the reinforcement in a spirally wound helix has greatly improved flexibility over the catheter tubing containing an internal wire stylet. The geometry of a helix wound "spring" has a much greater flexibility than a straight round wire stylet.

Still other objects and advantages of the invention will in part be apparent from the specification.

The invention accordingly comprises the features of construction, combination of elements, and arrangement of parts which will be exemplified in the construction hereinafter set forth, and the scope of the invention will be indicated in the claims.

DETAILED DESCRIPTION OF THE INVENTION

Figure 1:
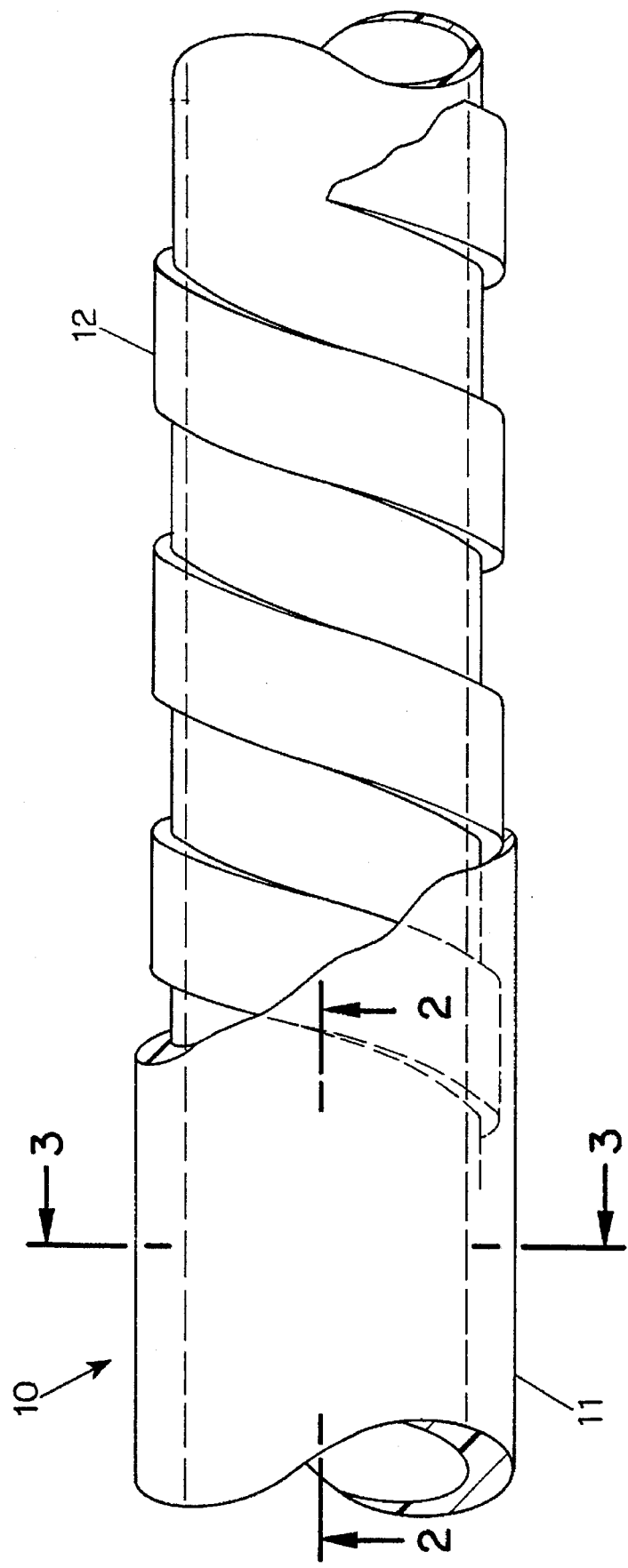
FIG. 1 is a front elevational view of the present invention embodied as a polymer resin tube containing a spirally wound reinforcement member imbedded within the tube walls.
Figure 1B:
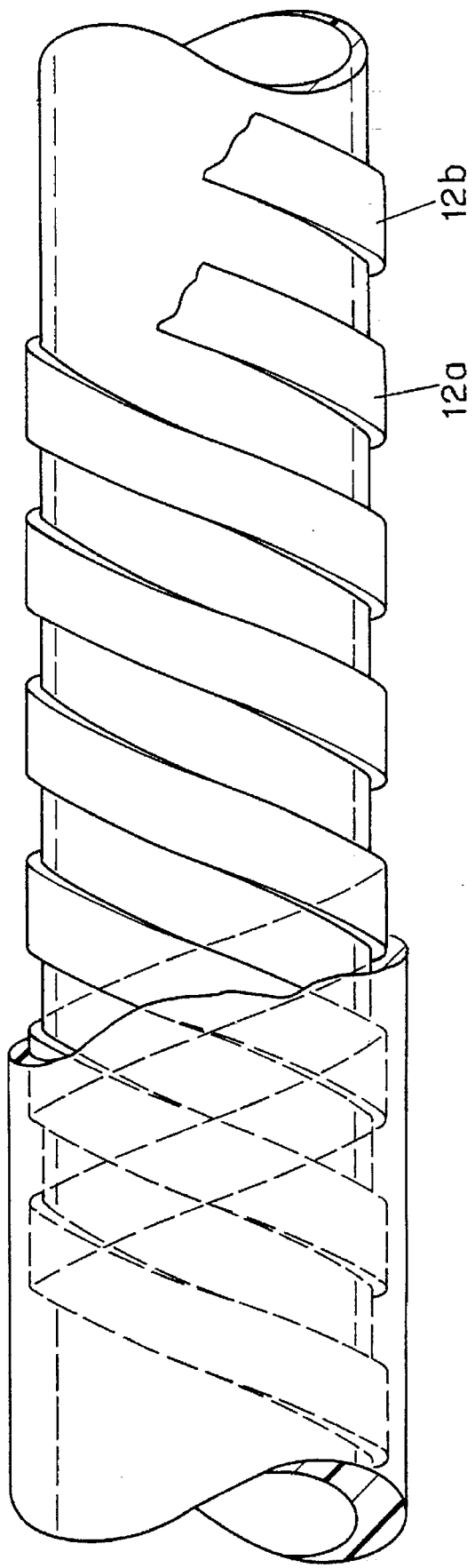
FIG. 1B is a front elevational view of the present invention embodied as a polymer resin tube containing a double strand spirally wound reinforcement member imbedded within the tube walls.
Figure 1C:
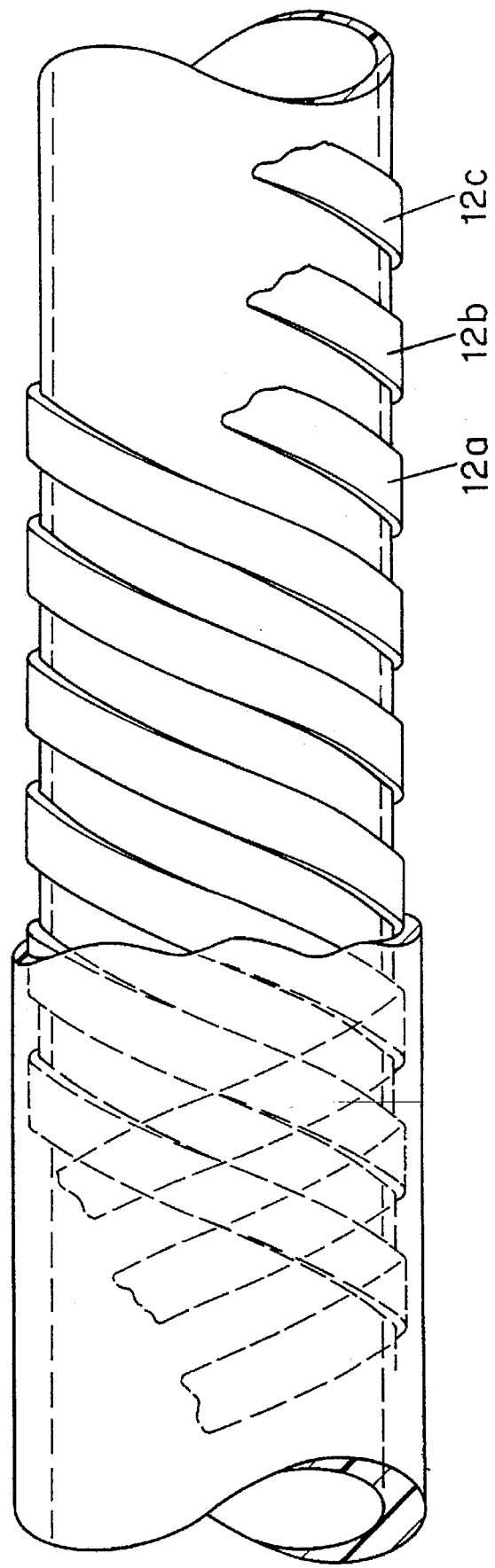
FIG. 1C is a front elevational view of the present invention embodied as a polymer resin tube containing a triple strand spirally wound reinforcement member imbedded within the tube walls.

FIG. 1 illustrates a polymer resin catheter tube 10 embodying features of this invention which generally comprises of the tube wall 11 containing an imbedded spirally wound reinforcement member 12. The reinforcement member is wound in a helix and does not overlap itself. In FIG. 1B a double strand reinforcement member is similarly wound from strands 12a and 12b. In FIG. 1C a triple strand reinforcement member is similarly wound from strands 12a, 12b and 12c.

Figure 2:
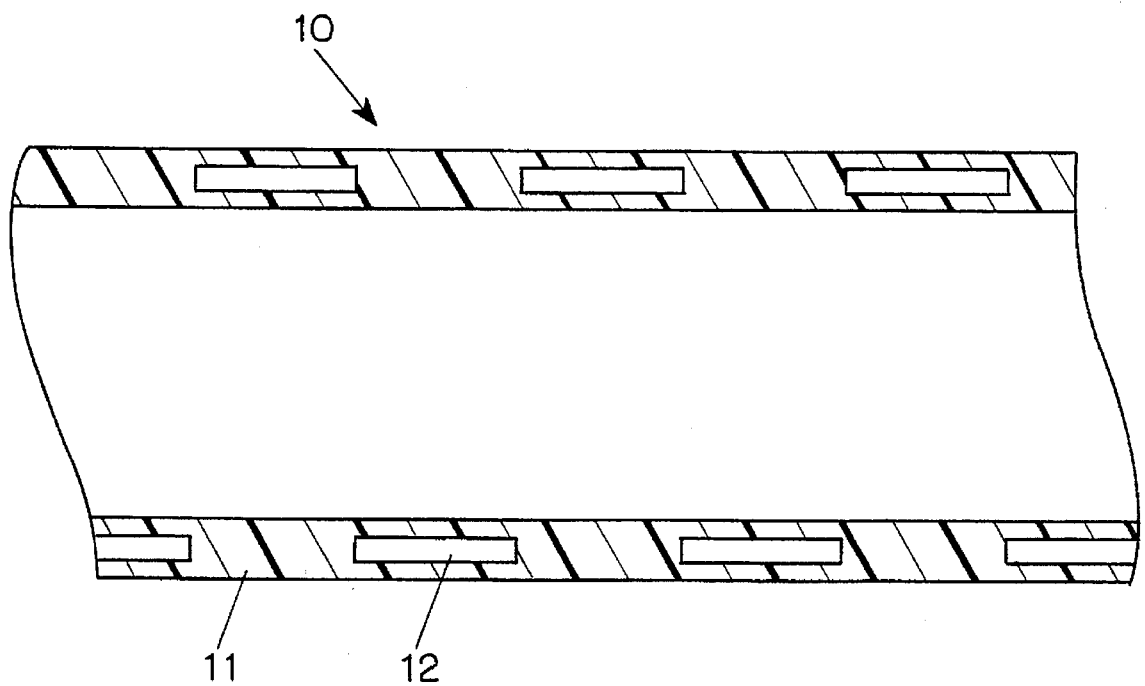
FIG. 2 is a longitudinal cross-sectional view taken along the lines 2—2 shown in FIG. 1.
Figure 3:
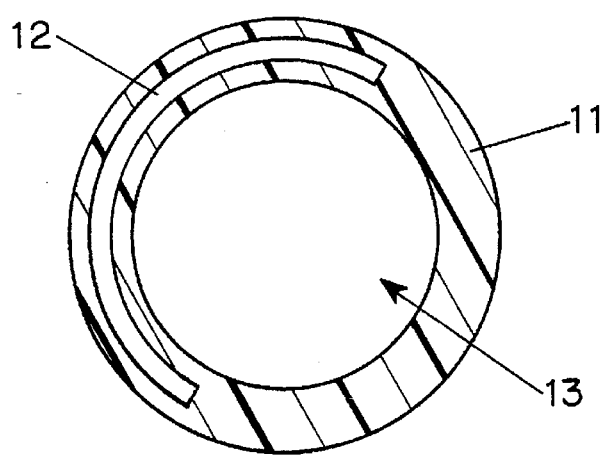
FIG. 3 is a transverse cross-sectional view taken along the lines 3—3 shown in FIG. 1.

FIGS. 2 and 3 illustrate the cross-sectional views of the tube 10 showing the reinforcement member 12 of this invention is fully encapsulated within the resin wall 11 of the tube 10. The outer surface of the tube 10 as well as the lumen of the tube 13 is circular in cross-section.

Figure 4A:
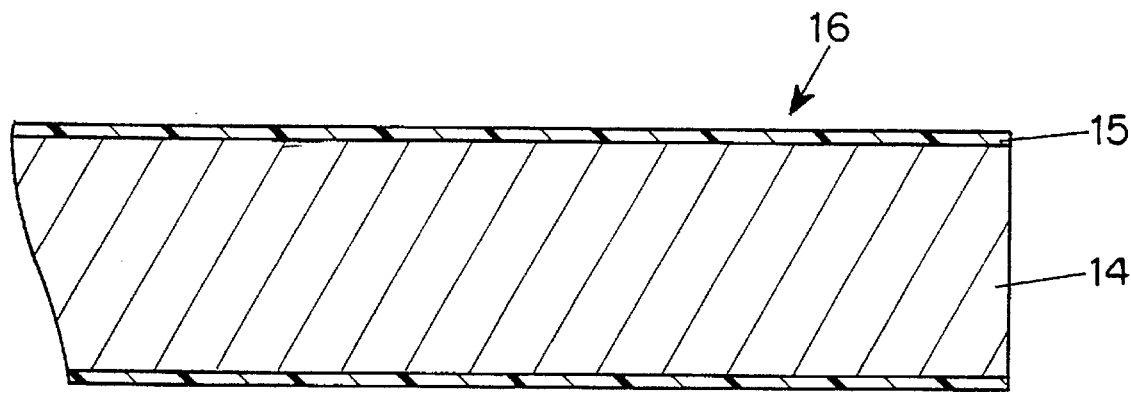
FIGS. 4A, 4B, and 4C illustrate the preferred method of forming the polymer resin catheter tube containing a spirally wound reinforcement member of flattened metal wire.
Figure 4B:
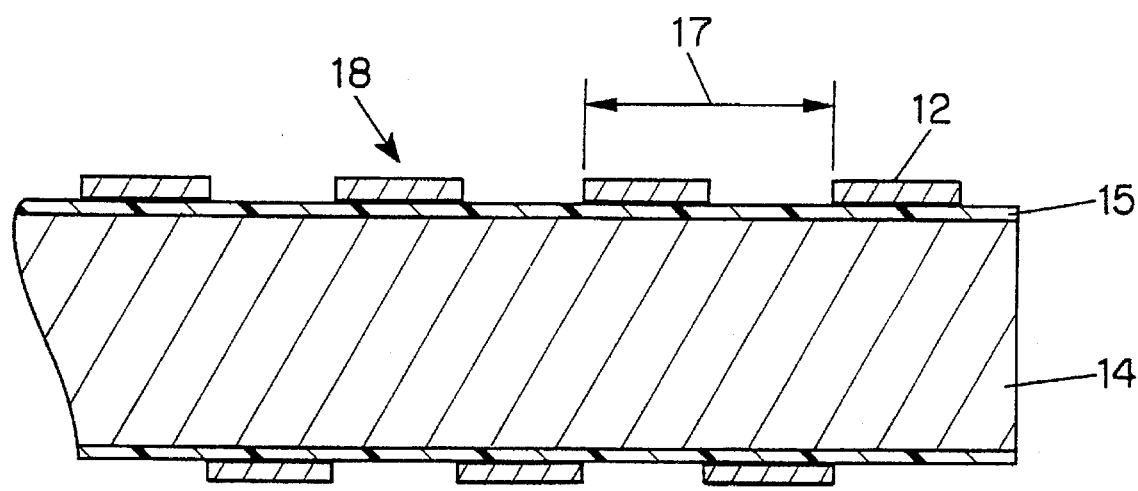
Figure 4C:
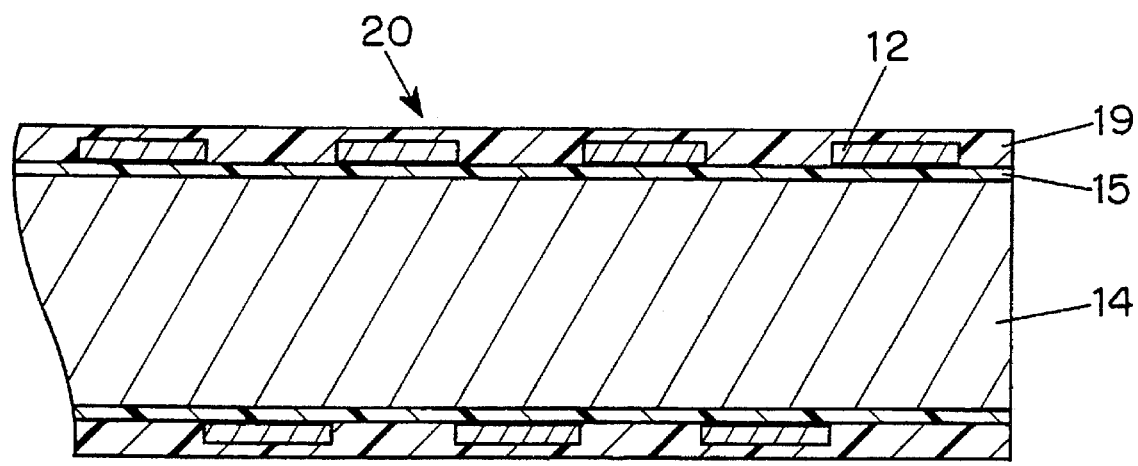

FIGS. 4A, 4B and 4C illustrate the manufacturing steps of this invention. Mandrel 14 in the preferred embodiment is annealed copper wire with a diameter equivalent to the final lumen diameter of the catheter tube 10. The wire can be from 0.002 inches to 0.100 inches in diameter depending on the final lumen diameter required. Copper wire is preferred because of its wide availability in different sizes, can be drawn with very tight diameter tolerance, is economical to use, can easily be recycled, and has a relatively low yield strength with a high elongation in tension. A mandrel material with high elongation is desirable in the preferred mandrel removal procedure described later in the process.

Mandrel 14 is coated with a base film of polymer resin 15 to form the base coated mandrel 16. The mandrel 14 used for this invention can be metallic or non-metallic, though in the preferred embodiment it is metallic. The considerations on the choice of mandrel material includes the method of removal in later operations, and the dimensional stability and tolerances it can maintain throughout the processing steps. The cross-section of the mandrel 14 is not limited to any particular shape. Any mandrel configuration such as (but not limited to) round, elliptical, square, or any polyhedral shape meeting the cross-sectional requirements of the finished tube 10 can be utilized as a suitable mandrel 14.

The base film 15 may be from any of the polymer resins such as the fluoropolymer family including, but not limited to, polyetetrafluoroethylenes (PTFE), the resin varnishes such as, but not limited to polyimides, polyamides, polyamidimides, polyurethanes, polyesters, etc., dispersion polymers or any other polymer material which can be applied to a mandrel or formed into a tube. The base film 15 may be a plurality of any of these polymers. The polymer utilized in the preferred embodiment of this invention is polyimide resin varnish.

Application of the base film 15 of polyimide in the preferred embodiment is by a dip and heat cure method with a mixture of polyamic acids and N-methyl-2-pyrrolidone. The base film 15 is formed by successive dipping and heat curing until an appropriate thickness is achieved on the mandrel 14 in the range of 0.00005 to 0.006 of an inch, depending on finished tube requirements. Application of a base film 15 can also be accomplished by other methods such as extrusion, electrodeposition, etc., dependent primarily upon the polymer system employed to form the base film or coating 15. FIG. 4A illustrates the longitudinal cross-section of the base coated mandrel 16.

Curing of the base film 15 can be accomplished by various processes dependent upon the polymer resin used. The techniques include heat, irradiation, chemical curing, etc. or a combination of these processes. The curing process must be compatible with the polymer resin system.

The reinforcement member 12 is applied to the base coated mandrel 16. Stainless steel was the chosen material for the reinforcement member 12 in the preferred embodiment due to its strength, radio-opacity and inert characteristics for medical applications. Other materials metallic, non-metallic or composites, depending upon desired characteristics, can also be used as reinforcement members 12.

In the preferred embodiment of this invention, a flattened (from round) stainless steel wire 12 is spirally wound in a single layer helix around the base coated mandrel 16. The flattened stainless steel reinforcement member 12 in the preferred embodiment measures approximately 0.001 inch (0.0254 mm) in thickness and approximately 0.007 inch (0.1178 mm) in width. The thickness and width of the reinforcement member 12 can range from 0.0002 inches to 0.005 inches in thickness and 0.002 inches to 0.100 in width.

In the preferred embodiment a flattened reinforcement member 12 is desired to obtain an increased width to thickness aspect ratio. This aspect ratio would allow a larger "X-ray shadow" for radiopacity while simultaneously minimizing the thickness required for the tube wall 11.

In the preferred embodiment of this invention, the 0.001 inch thickness of the reinforcement member 12 is desirable to minimize the total wall thickness of the finished tube 10. However the thickness can vary from 0.0002 to 0.005 of an inch.

Application of the reinforcement member 12 can be performed by various methods. In the preferred embodiment a single strand serving technique was utilized to wind the flattened stainless steel wire 12 around the base coated mandrel 16. Other techniques resulting in a similar configuration can also be employed. The direction of application of the reinforcement member 12 is not limited to any particular direction. The pitch 17 (period length per twist) of the applied reinforcement member 12 may be from just greater than 1× the width of the reinforcement member to 25× the width, and is preferably 1.5× to 3× the width of the reinforcement member. Lowering the pitch dimension 17 below 1× the reinforcement member width would result in adjacent members to be in contact or cause overlap. The minimum pitch dimension 17 would be based on the actual width or thickness dimension of the reinforcement member 12. In the preferred embodiment, a pitch dimension 17 of approximately 1.5 to 3 times the width of the flattened stainless steel reinforcement member 12. This pitch dimension 17 results in a coverage of approximately 33 to 67% of the surface area of the finished tube 10.

One embodiment of this invention utilizes a single strand of flattened stainless steel as the reinforcement member 12. Depending upon the final design and the dimensions of the reinforcement member, the preferred embodiment includes a plurality of radiopaque members may be applied to the base coated mandrel 16 as show in FIGS. 1A and 1B. The use of a plurality of radiopaque members or strands results is increased flexibility of the tube (over that of a tube with single strand of equivalent amount of material) without sacrificing strength or radiopacity.

The preassembly 18 illustrated in FIG. 4B consisting of the base coated mandrel 16 with the applied reinforcement member(s) 12 undergoes the next operation wherein the top coating 19 is applied. The material applied as the top coating 19 may be similar to the base coating 15, or it may be from a different family of polymer resins. The selection of polymer resins is the same as those listed above for the base coating 15, and the application and curing techniques are similarly applicable. In the preferred embodiment of this invention, the top coat layer 19 is the same polyimide resin utilized for the base coat layer 15. Application of the top coating 19 was performed by a dip and heat cure process to achieve the desired final tube wall thickness.

The subassembly 20 illustrated in FIG. 4C consists of the finished tube assembly 10 with the mandrel 14 still present within the lumen 13. All coating/filming processes have been completed on the final assembly 20 prior to proceeding with the next process to remove the mandrel 14.

To form the finished tube 10 from subassembly 20, the mandrel 14 must be removed. In the preferred embodiment of this invention the mandrel is removed by elongating the mandrel 14 beyond its elastic limit. This is accomplished by cutting subassembly 20 to a prescribed length and mechanically stripping away both ends of subassembly 20 to expose the mandrel 14. The stripping operation involves cutting through the top coating 19, the reinforcement member 12 and the base coat layer 15 without disturbing the mandrel 14. The mandrel is then mechanically elongated to approximately 120% of its original length by a method which applies tension to the exposed ends of mandrel 14. Elongation of the mandrel 14 will cause its diameter to decrease thereby separating it from the inner wall of the polymer resin tube assembly 10. The mandrel 14 can then be easily pulled from the spirally wrapped polymer tube 10.

There are various other methods to remove the mandrel 14, some of which are dependent upon the material chosen for the tube wall 11, the reinforcement member 12, and the mandrel 14. Of instance the mandrel 14 can be removed by subjecting the subassembly 20 to a solvent or other environment which will dissolve the mandrel 14 and not affect the polymer resin tube assembly 10 or the reinforcing member 12.

The mandrel 14 may be also be removed by subjecting subassembly 20 to a heated atmosphere at a temperature that will liquify or soften the mandrel 14 and not affect the polymer resin tube assembly 10 or the reinforcing member 12.

The mandrel 14 may also be removed by subjecting subassembly 20 to a temperature which will cause the mandrel 14 to contract more than the polymer resin tube 10. This can be accomplished if there is a sufficient difference in their respective coefficients of thermal expansion. The contraction of the mandrel 14 away from the polymer resin tube 10 will allow its removal.

Figure 5:
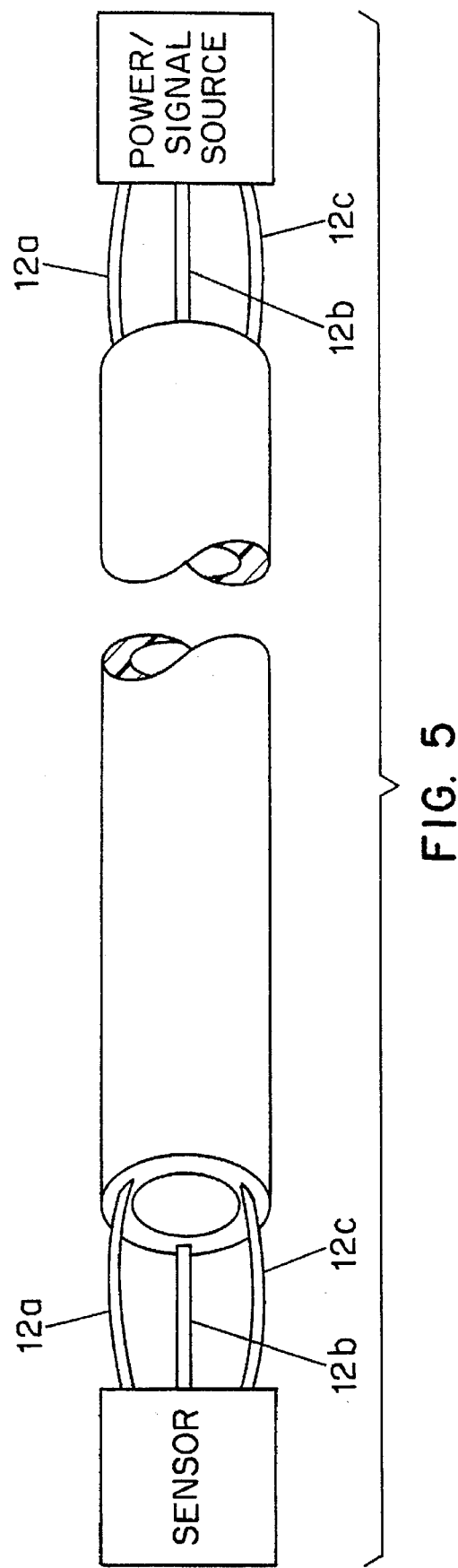
FIG. 5 schematically illustrates the triple strand embodiment attached to an external power/signal source at one end and a body sensor at the other.

As noted above, the reinforcement members are strands 12 of wire which extend from one end of the tube to the other and each strand does not cross itself or any other strand. In FIG. 5 it is shown how strands 12a, 12b and 12c can be used to conduct a signal from one end of the tube to the other. This might be important if the tube is to be used as a means for measuring temperature, oxygen or blood flow at the end of the catheter tube which has been inserted into the body. In such applications strand 12 can be attached to a miniature transducer or sensor at one end, and to an external power/ signal/gauge source at the other end. The strands 12a, 12b and 12c can run in a longitudinal direction instead of being wound in a helix.

It will thus be seen that the objects set forth above, among those made apparent from the preceding description, are efficiently attained and, since certain changes may be made in carrying out the above medical catheter tubing without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which is a matter of language might be said to fall therebetween.

What is claimed is:

1. A radiopaque tube for use as a medical catheter comprising:

an inner wall layer made from a polymer resin and defining a lumen;

a spiral wound reinforcement layer comprising a strand of a radiopaque material spirally wound about said inner wall layer so that said strand does not overlap itself or any other strand;

a polymer resin outer wall layer over said spiral wound reinforcement layer;

said sprial wound radiopaque layer being embedded between said inner wall layer and said outer wall layer; and sensor, power/signal, gauge or transducer means connected to at least one strand at either or both ends of the tube.

2. The tube of claim 1 wherein said radiopaque material is substantially flat wire.

* * * * *